United States Patent
Watanabe et al.

(10) Patent No.: US 11,045,098 B2
(45) Date of Patent: Jun. 29, 2021

(54) SENSOR

(71) Applicant: Nihon Kohden Corporation, Tokyo (JP)

(72) Inventors: Nobuyoshi Watanabe, Tokorozawa (JP); Takahiro Abe, Tokorozawa (JP); Hideki Fujisaki, Tokorozawa (JP); Kumi Sugiyama, Tokorozawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 246 days.

(21) Appl. No.: 15/935,335

(22) Filed: Mar. 26, 2018

(65) Prior Publication Data

US 2018/0279890 A1 Oct. 4, 2018

(30) Foreign Application Priority Data

Mar. 28, 2017 (JP) .............................. JP2017-063083

(51) Int. Cl.
*A61B 5/1455* (2006.01)
*A61B 5/022* (2006.01)
*A61B 5/00* (2006.01)

(52) U.S. Cl.
CPC ...... *A61B 5/02241* (2013.01); *A61B 5/14551* (2013.01); *A61B 5/14552* (2013.01); *A61B 5/6826* (2013.01); *A61B 2562/164* (2013.01); *A61B 2562/222* (2013.01); *A61B 2562/224* (2013.01)

(58) Field of Classification Search
None
See application file for complete search history.

(56) References Cited

U.S. PATENT DOCUMENTS

| | | | | |
|---|---|---|---|---|
| 5,964,701 A | * | 10/1999 | Asada | A61B 5/02438 600/300 |
| 6,845,256 B2 | * | 1/2005 | Chin | A61B 5/14552 600/323 |
| 6,916,289 B2 | * | 7/2005 | Schnall | A61B 5/6826 600/500 |
| 7,522,948 B2 | * | 4/2009 | Chin | A61B 5/14552 600/310 |
| 2012/0165688 A1 | * | 6/2012 | Liu | A61B 5/0006 600/500 |

(Continued)

FOREIGN PATENT DOCUMENTS

| | | |
|---|---|---|
| JP | H09-289977 A | 11/1997 |
| JP | 2007-029702 A | 2/2007 |

OTHER PUBLICATIONS

Lyew, MA, et al., "Blood pressure measurement using oscillometric finger cuffs in children and young adults", Anaesthesia, Oct. 1994, vol. 49, pp. 895-899, England.

(Continued)

*Primary Examiner* — Eric F Winakur
*Assistant Examiner* — Marjan Fardanesh
(74) *Attorney, Agent, or Firm* — Pearne & Gordon LLP

(57) ABSTRACT

A sensor includes a probe that acquires a blood light absorber concentration in a subject and a cuff that acquires a non-invasive blood pressure of the subject. In the sensor, the probe is configured to be attached to a first portion of a digit of the subject, and the cuff is configured to be attached to a second portion of the digit, the second portion being located on a periphery side with respect to the first portion.

17 Claims, 8 Drawing Sheets

(56) References Cited

U.S. PATENT DOCUMENTS

2013/0085356 A1\* 4/2013 Schlottau ............. A61B 5/6803
                                                    600/335
2018/0310891 A1\* 11/2018 Fine .................... A61B 5/0261

OTHER PUBLICATIONS

Ilies, C., et al., "Investigation of the agreement of a continuous non-invasive arterial pressure device in comparison with invasive radial artery measurement", British Journal of Anaesthesia, Feb. 2012, vol. 108, No. 2, pp. 202-210, England.
Extended European search report issued in Patent Application No. EP 18 16 4208 dated Jul. 30, 2018.

\* cited by examiner

SENSOR

CROSS REFERENCE TO RELATED APPLICATION

This application is based on. Japanese Patent Applications No. 2017-063083 filed on Mar. 28, 2017, the contents of which are incorporated herein by reference.

BACKGROUND

The presently disclosed subject matter relates to a sensor including a probe for acquiring the blood light absorber concentration in a subject and a cuff for acquiring the non-invasive blood pressure of the subject.

JP-A-2007-029702 discloses a probe which is to be attached to the fingertip of the subject. The probe includes a light emitter and a light detector. The light detector has a light-detecting surface for detecting a light beam that is emitted from the light emitter, and that is transmitted through tissue of the fingertip of the subject. The light detector is configured so as to output a signal corresponding to the intensity of the light beam which is received by the light-detecting surface. The wavelength of the light beam which is emitted from the light emitter is set to be absorbable by a material in blood. The volume of blood in the fingertip is changed by the pulsation, and therefore also the intensity of the light beam which is received by the light-detecting surface is changed. The signal which is output from the light detector is used for calculating vital signs information such as the pulse and the arterial oxygen saturation. The arterial oxygen saturation is used as an index indicating the rate of oxygen in blood as an example of the blood light absorber concentration.

In the case where measurements of the blood light absorber concentration and the non-invasive blood pressure are to be simultaneously performed on a subject, a cuff for acquiring the non-invasive blood pressure is usually wrapped around the upper arm of the subject.

In this case, a cable for a signal from the probe is drawn out from the fingertip portion of the subject, and a tube for supplying the air to the cuff is drawn out from the upper arm portion of the subject. The situation where the cable and the tube are drawn out from the separate body places of the subject may provide both the subject and the medical person with botheration.

The presently disclosed subject matter provides a sensor which reduces botheration applied to both the subject and the medical person in the case where measurements of the blood light absorber concentration and the non-invasive blood pressure are simultaneously performed on a subject.

SUMMARY

According to an aspect of the presently disclosed subject matter, a sensor includes:
a probe that acquires a blood light absorber concentration in a subject; and
a cuff that acquires a non-invasive blood pressure of the subject,
wherein the probe is configured to be attached to a first portion of a digit of the subject, and
the cuff is configured to be attached to a second portion of the digit, the second portion being located on a periphery side with respect to the first portion.

According to the above configuration, both the probe for acquiring the blood light absorber concentration in the subject, and the cuff for acquiring the non-invasive blood pressure of the subject are attached to the digit of the subject. Therefore, both a cable which is connected to the probe, and a tube which is connected to the cuff can be drawn out from the digit of the subject. It is possible to avoid a situation where the cable and the tube are drawn out from separate body places of the subject. In the case where measurements of the blood light absorber concentration and the non-invasive blood pressure are simultaneously performed on the subject, botheration which is applied to both the subject and the medical person can be reduced.

The acquisition of the blood light absorber concentration in the subject by the probe is performed based on a volume change of blood that is caused by pulsation of the subject in the digit to which the probe is attached. According to the configuration, the second portion of the digit to which the cuff is attached is located on the periphery side with respect to the first portion to which the probe is attached. Even when the cuff compresses the second portion of the digit to acquire the non-invasive blood pressure, the pulsation of the artery in the first portion which is necessary for the probe to acquire the blood light absorber concentration is not inhibited. In the case where measurements of the blood light absorber concentration and the non-invasive blood pressure are simultaneously performed on the subject, decrease in the accuracy of the acquired blood light absorber concentration is avoidable, and moreover the blood light absorber concentration can be continuously measured.

According to an aspect of the presently disclosed subject matter, a sensor includes:
a probe that acquires a blood light absorber concentration in a subject; and
a cuff that acquires a non-invasive blood pressure of the subject,
wherein the probe is configured to be attached to a first digit of the subject, and
the cuff is configured to be attached to a second digit of the subject.

According to the configuration, both the probe for acquiring the blood light absorber concentration in the subject, and the cuff for acquiring the non-invasive blood pressure of the subject are attached to the digits of the subject. Therefore, both a cable which is connected to the probe, and a tube which is connected to the cuff can be drawn out from the hand or foot of the subject. It is possible to avoid a situation where the cable and the tube are drawn out from separate body places of the subject. In the case where measurements of the blood light absorber concentration and the non-invasive blood pressure are simultaneously performed on the subject, botheration which is applied to both the subject and the medical person can be reduced.

The acquisition of the blood light absorber concentration in the subject by the probe is performed based on a volume change of blood that is caused by pulsation of the subject in the digit to which the probe is attached. According to the configuration, the probe and the cuff are attached to different digits, and therefore placed to different peripheral blood vessels from each other. Even when the cuff compresses peripheral blood vessels in the second digit to acquire the non-invasive blood pressure, the pulsation of the artery in the first digit which is necessary for the probe to acquire the blood light absorber concentration is not inhibited. In the case where measurements of the blood light absorber concentration and the non-invasive blood pressure are simultaneously performed on the subject, decrease of the accuracy of the acquired blood light absorber concentration is avoidable, and moreover the blood light absorber concentration can be continuously measured.

DETAILED DESCRIPTION OF EMBODIMENTS

Figure 1:
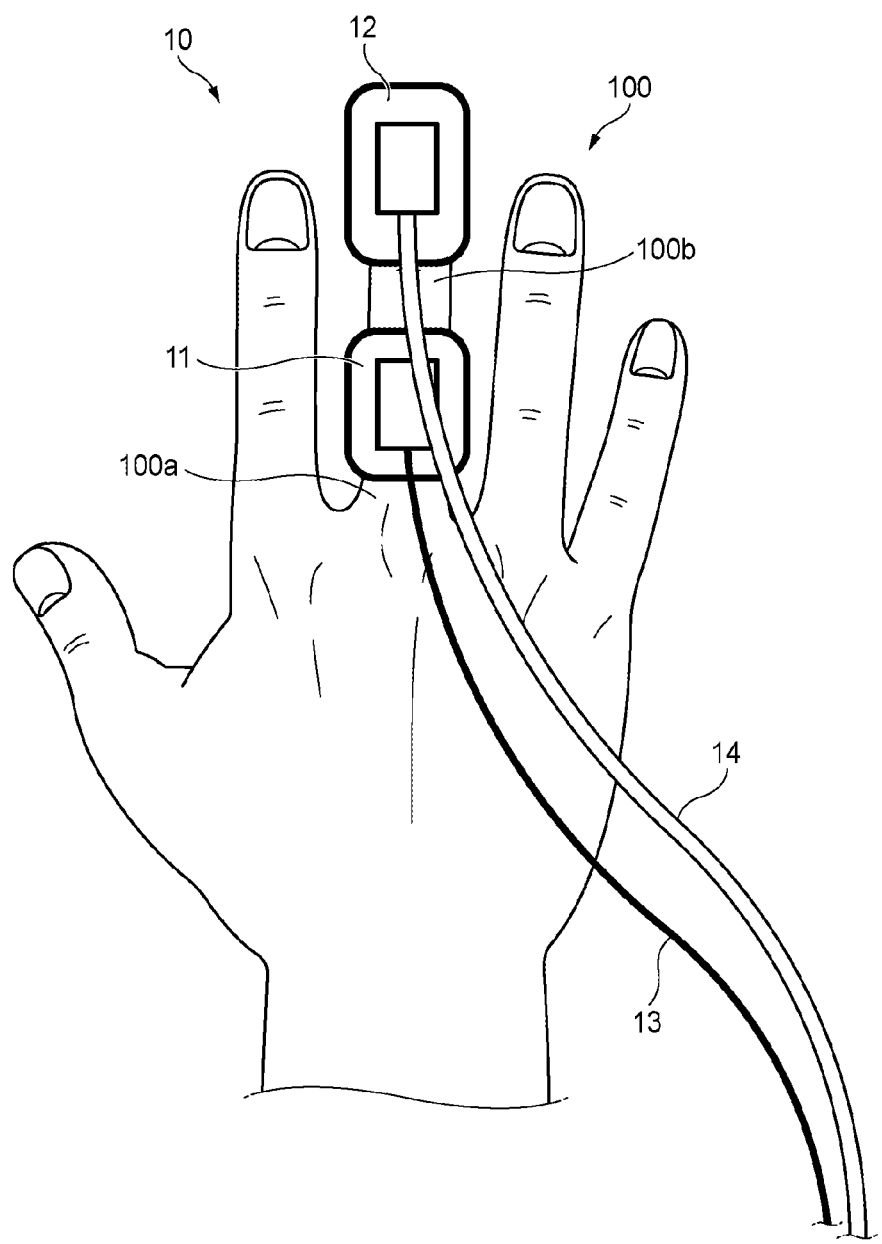
FIG. 1 illustrates an attachment state of a sensor in a first embodiment to a subject.

Hereinafter, embodiment examples will be described in detail with reference to the accompanying drawings. FIG. 1 illustrates a state in which a sensor 10 of a first embodiment is attached to a hand finger 100 of a subject.

The sensor 10 includes a probe 11 and a cuff 12. The probe 11 is a device for acquiring the arterial oxygen saturation (an example of the blood light absorber concentration) of the subject. The cuff 12 is a device for acquiring the non-invasive blood pressure of the subject.

Figure 2A:
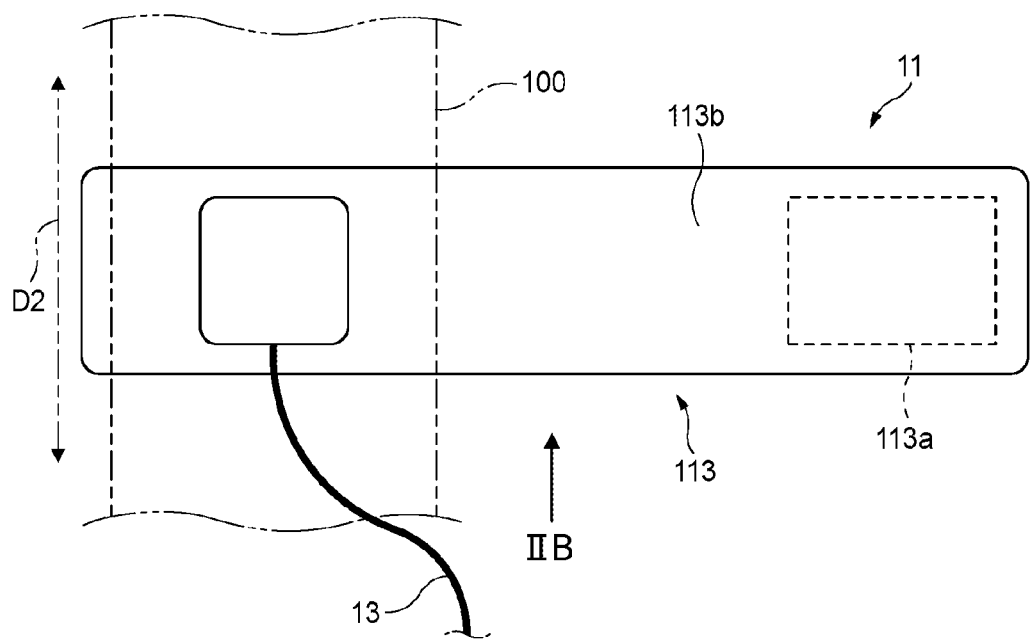
FIGS. 2A and 2B illustrate the configuration of a probe of the sensor of FIG. 1.
Figure 2B:
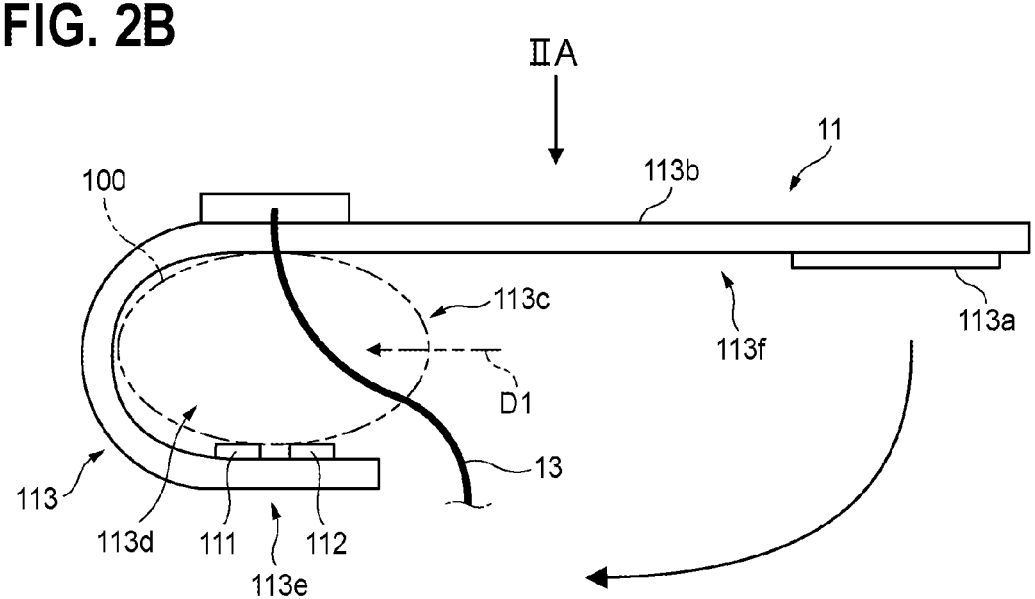

FIGS. 2A and 2B schematically illustrate the configuration of the probe 11. FIG. 2A shows the configuration as viewed in the direction of the arrow 11A in FIG. 2B. FIG. 2B illustrates the configuration as viewed in the direction of the arrow 11B in FIG. 2A.

As shown in FIG. 2B, the probe 11 includes a light emitter 111, a light detector 112, and a support member 113.

The light emitter 111 is configured so as to emit a red light beam and an infrared light beam. For example, the light emitter 111 is a semiconductor light emitting device configured to emit light beams of the predetermined wavelengths. The semiconductor light emitting device may be a light emitting diode (LED), a laser diode, or an organic EL device.

The light detector 112 has a light-detecting surface which is configured to detect a light beam transmitted through or reflected from a living tissue of the subject. The light detector 112 is configured so as to output an intensity signal based on the intensity of the light beam which is received by the light-detecting surface. The volume of blood in the living tissue to which the probe 11 is attached is changed by the pulsation of the subject. Therefore, the intensity of the light beam which is received by the light-detecting surface is changed, and also the intensity signal which is output from the light detector 112 is changed.

For example, the light detector 112 is an optical sensor having a sensitivity to the above-described predetermined wavelengths. The optical sensor may be a photodiode, a phototransistor, or a photoresistor.

The light emitter 111 and the light detector 112 are supported by the support member 113 having a belt-like shape. The support member 113 has a hook surface 113a and loop surface 113b which form a hook and loop fastener. The probe 11 is configured so as to be used while the support member is wound around the hand finger 100. The hook surface 113a is fixed at an adequate position of the loop surface 113b, thereby the light emitter 111 and the light detector 112 are closely contacted with the hand finger 100.

The sensor 10 further includes a cable 13. One end of the cable 13 is connected to the probe 11. The other end of the cable 13 is to be connected to a vital sign measurement apparatus which is not shown in the drawings. The cable 13 may include a power supply line for supplying an electric power to the light emitter 111 and the light detector 112, a signal line for transmitting the intensity signal output from the light detector 112, and the like. The cable 13 may be inseparably integrated with the probe 11, or attachable to and detachable from the probe 11.

Figure 3A:
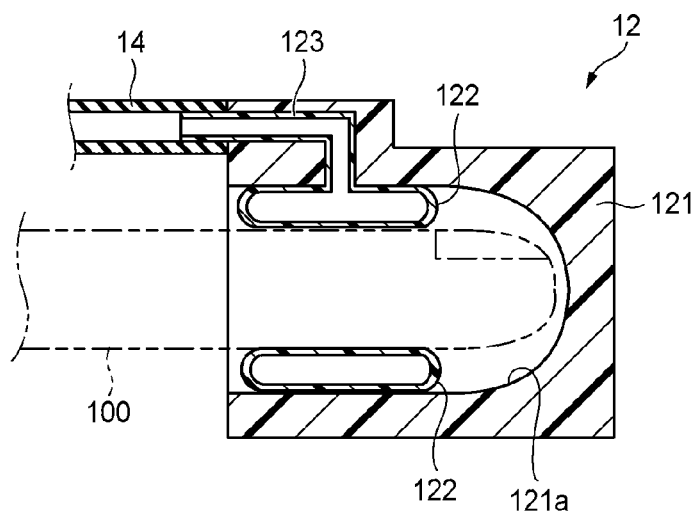
FIGS. 3A and 3B illustrate the configuration of a cuff of the sensor of FIG. 1.

FIG. 3A is a sectional view schematically illustrating the configuration of the cuff 12. The cuff 12 includes a case 121, an annular bag member 122, and an air passage 123. The case 121 has a bottomed hole 121a. The bag member 122 is accommodated in the hole 121a. The outer circumferential surface of the bag member 122 is fixed to the inner circumferential surface of the hole 121a. The air passage 123 communicates with the interior of the bag member 122.

When the cuff 12 is used, the hand finger 100 of the subject is inserted into the hole 121a. At this time, the inner circumferential surface of the bag member 122 surrounds the hand finger 100.

As shown in FIG. 1, the sensor 10 further includes a tube 14. As shown in FIG. 3A, one end of the tube 14 is connected to the air passage 123 of the cuff 12. The other end of the tube 14 is to be connected to the vital sign measurement apparatus which is not shown in the drawings. The tube 14 may be inseparably integrated with the cuff 12, or attachable to and detachable from the cuff 12.

The tube 14 is used for supplying the air to the cuff 12. Specifically, the amount of the air which is supplied to the interior of the bag member 122 through the air passage 123 is adjusted based on a blood pressure measurement operation in the vital sign measurement apparatus. This causes the force with which the hand finger 100 is compressed by the bag member 122 in order to acquire the the non-invasive blood pressure of the subject, to be adjusted.

As shown in FIG. 1, the probe 11 is attached to a root portion 100a of the hand finger 100. In other words, the shape and dimensions of the probe 11 which has been described with reference to FIG. 2 are configured so that the probe is attached to the root portion 100a (an example of the first portion of the digit) of the hand finger 100.

On the other hand, the cuff 12 is attached to a fingertip portion 100b of the hand finger 100. In other words, the shape and dimensions of the cuff 12 which has been described with reference to FIG. 3A are configured so that the cuff is attached to the fingertip portion 100b (an example of the second portion of the digit) of the hand finger 100. The fingertip portion 100b is defined as a portion which is located on the periphery side with respect to the root portion 100a.

In the embodiment, both the probe 11 for acquiring the arterial oxygen saturation of the subject, and the cuff 12 for acquiring the non-invasive blood pressure of the subject are attached to the hand finger 100 of the subject. This allows both the cable 13 which is connected to the probe 11, and the tube 14 which is connected to the cuff 12, to be drawn out from the hand finger 100 of the subject as shown in FIG. 1. It is possible to avoid a situation where the cable and the tube are drawn out from separate body places of the subject. In the case where measurements of the arterial oxygen saturation and the non-invasive blood pressure are simultaneously performed on the subject, therefore, botheration which is applied to both the subject and the medical person can be reduced.

As described above, the acquisition of the arterial oxygen saturation of the subject by the probe 11 is performed based on a volume change of blood that is caused by pulsation of the subject in the hand finger 100 to which the probe 11 is attached. In the embodiment, the portion of the hand finger 100 to which the cuff 12 is attached is located on the periphery side with respect to the portion of the hand finger 100 to which the probe 11 is attached. Even when the bag member 122 of the cuff 12 compresses the fingertip portion 100b to acquire the non-invasive blood pressure, the pulsation of the artery in the root portion 100a which is necessary for the probe 11 to acquire the arterial oxygen saturation is not inhibited. In the case where measurements of the arterial oxygen saturation and the non-invasive blood pressure are simultaneously performed on the subject, decrease in the accuracy of the acquired arterial oxygen saturation is avoidable, and moreover the arterial oxygen saturation can be continuously measured.

Figure 3B:
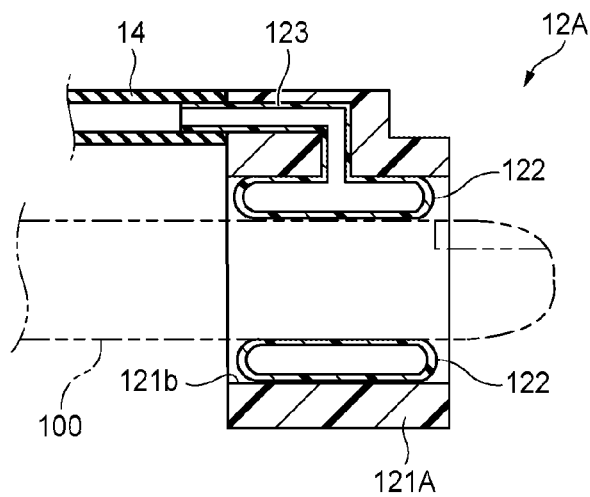

In the embodiment, as shown in FIG. 3A, the cuff 12 includes the case 121 in which the bottomed hole 121a is formed. The hand finger 100 of the subject is to be inserted into the bottomed hole 121a. A configuration such as a cuff 12A of a modification shown in FIG. 3B may be used. The cuff 12A has a case 121A. The case 121A has a through hole 121b through which the fingertip of the hand finger 100 of the subject is passable. Components which are substantially identical with those of the sensor 10 of the cuff 12 are denoted by the same reference numerals.

Figure 4:
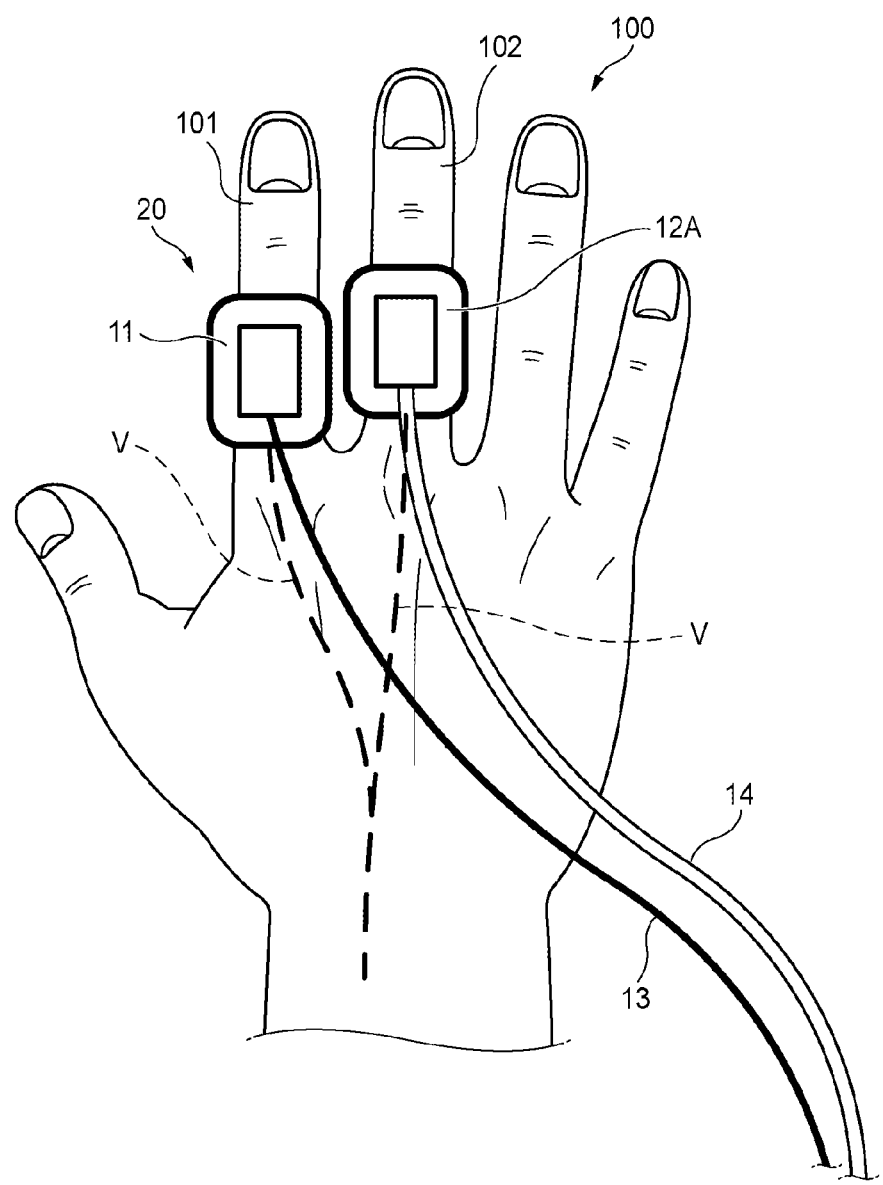
FIG. 4 illustrates an attachment state of a sensor in a second embodiment to the subject.

FIG. 4 illustrates a state where a sensor 20 of a second embodiment is attached to the hand finger 100 of the subject. Components which are substantially identical with those of the sensor 10 of the first embodiment are denoted by the same reference numerals, and repeated description is omitted.

The sensor 20 includes the probe 11 and the cuff 12A. The hand finger 100 of the subject includes the index finger 101 and the middle finger 102. The probe 11 is attached to the index finger 101 (an example of the first digit) of the subject. The cuff 12A is attached to the middle finger 102 (an example of the second digit) of the subject.

Also in the embodiment, both the probe 11 for acquiring the arterial oxygen saturation of the subject, and the cuff 12A for acquiring the non-invasive blood pressure of the subject are attached to the hand finger 100 of the subject. This allows both the cable 13 which is connected to the probe 11, and the tube 14 which is connected to the cuff 12A, to be drawn out from the hand of the subject as shown in FIG. 4. It is possible to avoid a situation where the cable and the tube are drawn out from separate body places of the subject. In the case where measurements of the arterial oxygen saturation and the non-invasive blood pressure are simultaneously performed on the subject, therefore, botheration which is applied to both the subject and the medical person can be reduced.

As described above, the acquisition of the arterial oxygen saturation of the subject by the probe 11 is performed based on a volume change of blood that is caused by pulsation of the subject in the hand finger 100 to which the probe 11 is attached. In the embodiment, the probe 11 and the cuff 12A are attached to the different fingers, and therefore respectively placed above different peripheral blood vessels V. Even when the bag member 122 of the cuff 12A compresses the peripheral blood vessel in the middle finger 102 to acquire the non-invasive blood pressure, the pulsation of the artery in the index finger 101 which is necessary for the probe 11 to acquire the arterial oxygen saturation is not inhibited. In the case where measurements of the arterial oxygen saturation and the non-invasive blood pressure are simultaneously performed on the subject, decrease of the accuracy of the acquired arterial oxygen saturation is avoidable, and moreover the arterial oxygen saturation can be continuously measured.

In the embodiment, the probe 11 is attached to the index finger 101, and the cuff 12A is attached to the middle finger 102. However, the probe 11 and the cuff 12A can be attached to any fingers of the hand as far as the hand fingers to which the probe and the cuff are to be attached are different from each other. In place of the cuff 12A, the cuff 12 shown in FIG. 3A may be used.

In the above-described embodiments, as shown in FIG. 2B, the support member 113 of the probe 11 defines a space 113d having an opening 113c. When the probe 11 is attached to the hand finger 100 of the subject, the hand finger 100 can enter the space 113d from the opening 113c in a direction D1. The direction D1 is a direction intersecting with a direction D2 which is indicated in FIG. 2A, and along which the hand finger 100 extends.

According to the configuration, in the case where measurements of the arterial oxygen saturation and the non-invasive blood pressure are simultaneously performed on the subject, the work of attaching the probe 11 to the hand finger 100 can be facilitated. In the case where the cuff 12 is attached on the periphery side with respect to the probe 11 as in the example shown in FIG. 1, particularly, the effect is remarkable. In attachment of the probe 11, it is not necessary to consider the attachment sequence with respect to the cuff 12, or to once detach the cuff 12.

As shown in FIG. 2B, the support member 113 has a first support portion 113e and a second support portion 113f. The first support portion 113e includes a part which supports at least the light emitter 111 and the light detector 112. The second support portion 113f includes at least a part for fixing the first support portion 113e to the hand finger 100. The second support portion 113f has a flexibility which is higher than that of the first support portion 113e. In other words, the first support portion 113e is more robust than the second support portion 113f.

According to the configuration, the light emitter 111 and the light detector 112 are supported by the more robust part, and therefore positional displacement of the light emitter 111 and the light detector 112 with respect to the hand finger 100 is easily reduced. On the other hand, the first support portion 113e is fixed to the hand finger 100 by the second support portion 113f which is more flexible. Consequently, the light emitter 111 and the light detector 112 can be closely attached to the hand finger. Therefore, the accuracy of the acquired arterial oxygen saturation can be improved.

In the support member 113, at least the first support portion 113e may be formed by a shape-memory material such as a shape-memory resin, a shape-memory alloy, or a shape-memory ceramic. The temperature functioning as the reference for shape memory may be ordinary temperature or body temperature.

According to the configuration, the space 113d which is defined by the support member 113 can be maintained to have a shape which is adequate for receiving the hand finger 100. Consequently, the light emitter 111 and the light detector 112 can be closely attached the hand finger 100. Therefore, the accuracy of the acquired arterial oxygen saturation can be improved.

Figure 5:
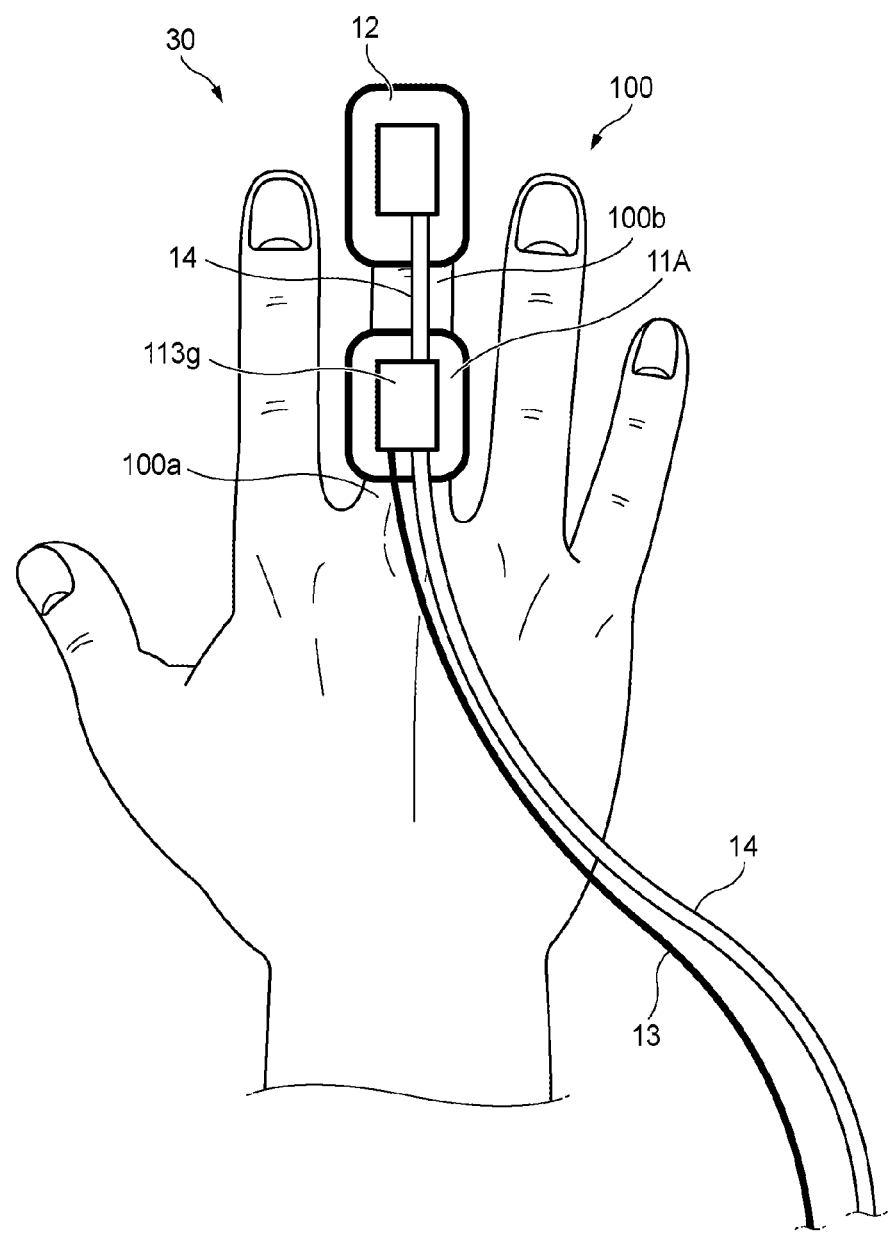
FIG. 5 illustrates an attachment state of a sensor in a third embodiment to the subject.

FIG. 5 illustrates a state where a sensor 30 of a third embodiment is attached to the hand finger 100 of the subject. Components which are substantially identical with those of the sensor 10 of the first embodiment are denoted by the same reference numerals, and repeated description is omitted.

The sensor 30 includes a probe 11A and the cuff 12. The probe 11A is a device for acquiring the arterial oxygen saturation of the subject.

Figure 6A:
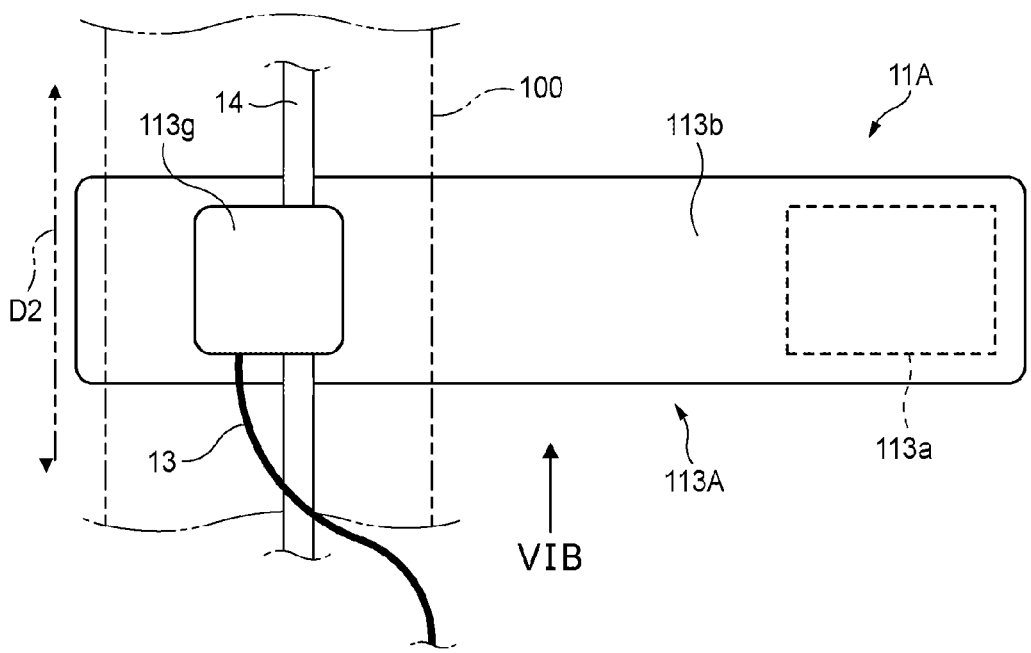
FIGS. 6A and GB illustrate the configuration of a probe of the sensor of FIG. 5.
Figure 6B:
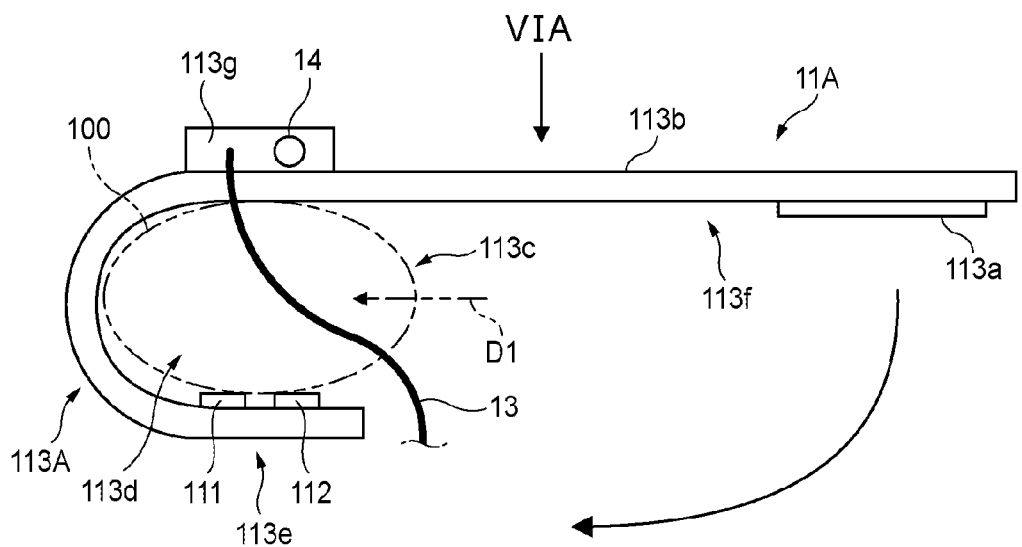

FIGS. 6A and 6B schematically illustrate the configuration of the probe 11A. FIG. 6A illustrates the configuration as viewed in the direction of the arrow VIA in FIG. 6B. FIG. 6B illustrates the configuration as viewed in the direction of the arrow VIB in FIG. 6A.

The probe 11A includes a support member 113A. The support member 113A includes a tube support portion 113g. The tube support portion 113g supports the tube 14 for supplying the air to the cuff 12. The tube support portion 113g may be structured so as to be detachable from the support member 113A by forming a hook surface which forms a hook and loop fastener, on a surface of the tube support portion 113g that is opposed to the loop surface 113b of the support member 113A.

According to the configuration, as shown in FIG. 5, the probe 11A which is to be attached to the hand finger 100 in order to acquire the arterial oxygen saturation of the subject may be caused to function as a fixing device for the tube 14 connected to the cuff 12. Therefore, the drawn-out directions of the cable 13 and tube 14 which are drawn out from different places of the hand 100 can be easily aligned with each other. In the case where measurements of the arterial oxygen saturation and the non-invasive blood pressure are simultaneously performed on the subject, botheration which is applied to both the subject and the medical person can be further reduced.

The tube support portion 113g may be immovable with respect to the tube 14, or slidable along the tube 14. In the latter case, the attachment position of the probe 11A can be appropriately adjusted while maintaining the integrality with the cuff 12. Therefore, decrease of the accuracy of the acquired arterial oxygen saturation is avoidable.

Figure 7:
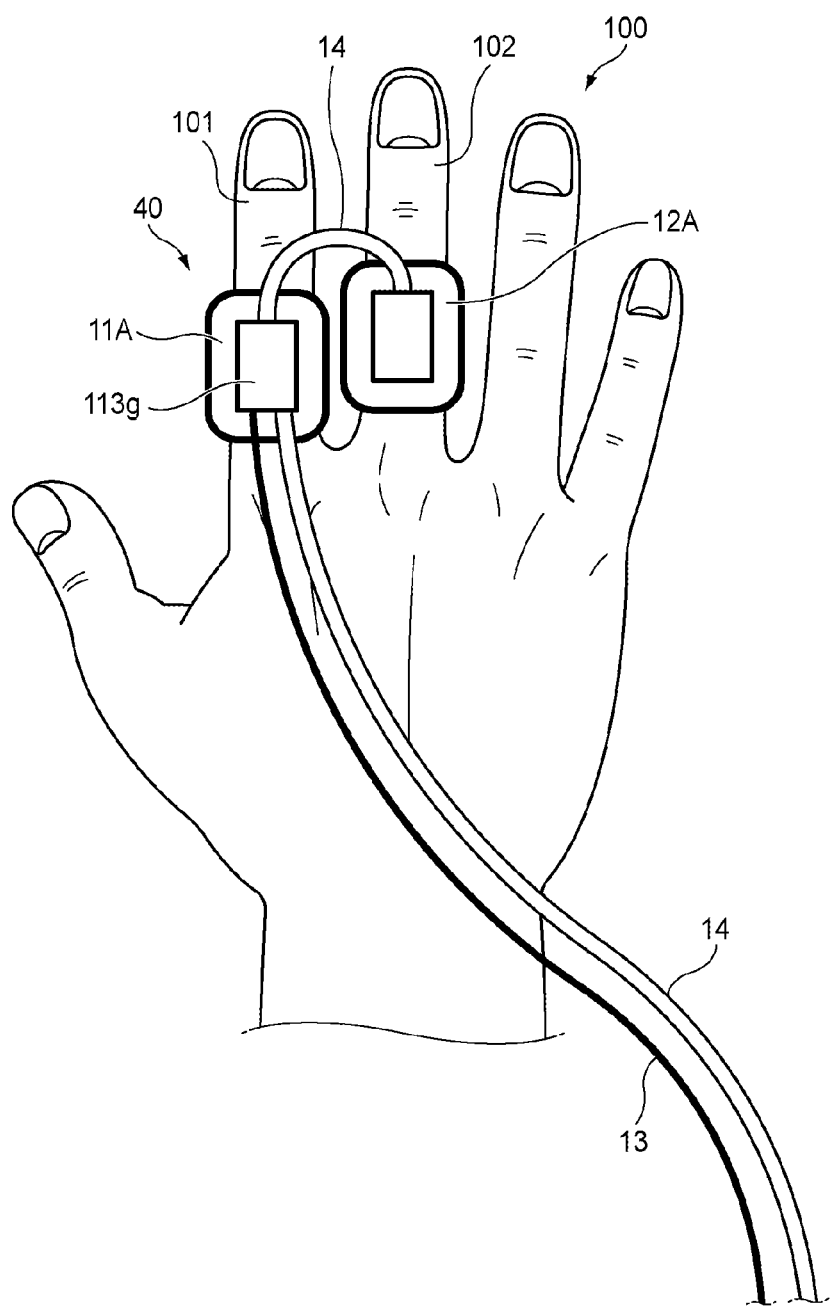
FIG. 7 illustrates an attachment state of a sensor in a fourth embodiment to the subject.

FIG. 7 illustrates a state where a sensor 40 of a fourth embodiment is attached to the hand finger 100 of the subject. Components which are substantially identical with those of the sensor 20 of the second embodiment and the sensor 30 of the third embodiment are denoted by the same reference numerals, and repeated description is omitted.

The sensor 40 includes the probe 11A and the cuff 12A. The tube support portion 113g of the probe 11a supports the tube 14 for supplying the air to the cuff 12A.

According to the configuration, the probe 11A which is to be attached to the hand finger 100 in order to acquire the arterial oxygen saturation of the subject may be caused to function as a fixing device for the tube 14 connected to the cuff 12A. Therefore, the drawn-out directions of the cable 13 and tube 14 which are drawn out from different hand fingers can be easily aligned with each other. In the case where measurements of the arterial oxygen saturation and the non-invasive blood pressure are simultaneously performed on the subject, therefore, botheration which is applied to both the subject and the medical person can be further reduced.

Figure 8:
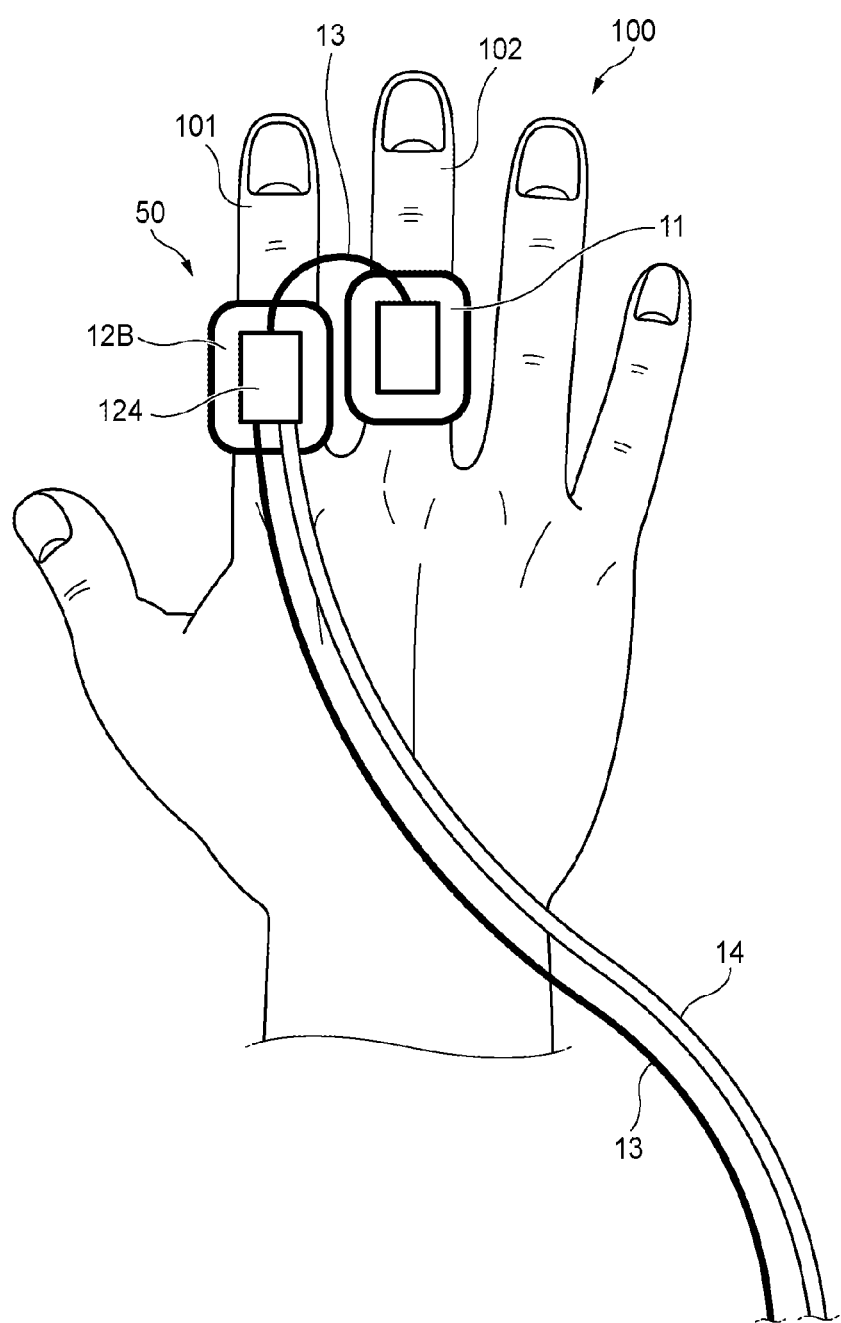
FIG. 8 illustrates an attachment state of a sensor in a fifth embodiment to the subject.

FIG. 8 illustrates a state where a sensor 50 of a fifth embodiment is attached to the hand finger 100 of the subject. Components which are substantially identical with those of the sensor 10 of the first embodiment are denoted by the same reference numerals, and repeated description is omitted.

The sensor 50 includes the probe 11 and a cuff 12B. The probe 11 is attached to the middle finger 102 (an example of the first digit) of the subject, and the cuff 12B is attached to the index finger 101 (an example of the second digit) of the subject.

The cuff 12B is a device for acquiring the non-invasive blood pressure of the subject. The basic configuration of the cuff 12B may be similar to that of the cuff 12 shown in FIG. 3A or that of the cuff 12A shown in FIG. 3B. The cuff 12B is different from the cuff 12 and the cuff 12A in that the cuff 12B includes a cable support portion 124. The cable support portion 124 supports the cable 13 connected to the probe 11.

According to the configuration, the cuff 12B which is to be attached to the hand finger 100 in order to acquire the non-invasive blood pressure may be used as a fixing device for the cable 13 connected to the probe 11. Therefore, the drawn-out directions of the cable 13 and tube 14 which are drawn out from different fingers can be easily aligned with each other. In the case where measurements of the arterial oxygen saturation and the non-invasive blood pressure are simultaneously performed on the subject, therefore, botheration which is applied to both the subject and the medical person can be further reduced.

The above-described embodiments is for facilitating understanding of the invention, and do not limit the invention. It is obvious that the configuration may be changed or improved without deviation from the point of the invention, and its equivalents are included within the scope of the invention.

In the above-described embodiments, the probe for acquiring the arterial oxygen saturation, and the cuff for acquiring the non-invasive blood pressure are attached to a hand finger(s) of the subject. However, the probe and the cuff may be configured so as to be attached to toes of the foot of the subject.

In the above-described embodiments, the probe is used for acquiring the arterial oxygen saturation. However, the probe may have a configuration for acquiring a blood light absorber, such as the concentration of carboxyhemoglobin, methemoglobin, or the like.

In the above-described embodiments, the light emitter 111 is configured so as to emit a red light beam and an infrared light beam. However, the light emitter 111 may be configured so as to further emit a blue light beam, a green light beam, an orange light beam, a red-orange light beam, or the like.

What is claimed is:
1. A sensor comprising:
   a probe comprising:
      a light emitter,
      a light detector, and
      a support member that supports the light emitter and the light detector, the support member having a shape which is curved to have an open portion;
   a cuff; and
   a tube that supplies air to the cuff, wherein the tube is supported by the support member of the probe,
   wherein the probe is configured to be attached to a first portion of a digit of a subject,
   wherein the cuff is configured to be attached to a second portion of the digit, the second portion being located on a fingertip side with respect to the first portion, and
   wherein the support member includes:

a first support portion that supports the light emitter and the light detector; and
a second support portion that is higher in flexibility than the first support portion, and that is used for fixing the first support portion to the first portion of the digit.

2. The sensor according to claim 1, wherein the support member is made of a shape-memory material.

3. The sensor according to claim 1, wherein the first portion is located at a base portion of the digit and the second portion is located at a tip of the digit.

4. The sensor according to claim 1, wherein the first portion is located closer to a base of the digit than the second portion.

5. The sensor according to claim 1, wherein the second portion is located distal to the first portion.

6. The sensor according to claim 1, wherein the cuff comprises a bag member.

7. The sensor according to claim 6, wherein the tube is connected to the cuff such that the tube supplies air to an interior of the bag member.

8. The sensor according to claim 6, wherein the bag member is annular.

9. The sensor according to claim 6, wherein the cuff further comprises a case defining a hole, and the bag member is accommodated in the hole of the case.

10. The sensor according to claim 1, wherein:
the cuff is configured for acquiring a non-invasive blood pressure of the subject, and
the probe is configured for acquiring a blood light absorber concentration in the subject.

11. The sensor according to claim 1, wherein the support member has a first end and a second end that is movable relative to the first end.

12. A sensor comprising:
a probe comprising:
a light emitter,
a light detector, and
a support member that supports the light emitter and the light detector;
a cuff; and
a tube for supplying air to the cuff, the tube being supported by the support member of the probe,
wherein the probe is configured to be attached to a first portion of a digit of a subject,
wherein the cuff is configured to be attached to a second portion of the digit, the second portion being located on a fingertip side with respect to the first portion, and
wherein the support member includes a first support portion and a second support portion that is releasably attachable to the first support portion to fix the support member to the first portion of the digit.

13. The sensor according to claim 12, wherein:
the first support portion defines a space for receiving the first portion of the digit,
the second support portion is releasably attachable to the first support portion to selectively adjust the support member between a first configuration and a second configuration,
wherein under the first configuration, the second support portion is spaced from the first support portion such than an opening is provided between the first support portion and second support portion that permits entry of the first portion of the digit through the opening and into the space, and
wherein under the second configuration, the second support portion is releasably attached to the first support portion such the support member forms a closed loop that surrounds the space.

14. The sensor according to claim 12, wherein the support member has a first end and a second end that is movable relative to the first end.

15. The sensor according to claim 12, wherein:
the cuff is configured for acquiring a non-invasive blood pressure of the subject, and
the probe is configured for acquiring a blood light absorber concentration in the subject.

16. A sensor comprising:
a probe comprising:
a light emitter,
a light detector, and
a support member that supports the light emitter and the light detector, the support member having a first end and a second end that is movable relative to the first end;
a cuff; and
a tube for supplying air to the cuff, the tube being supported by the support member of the probe,
wherein the probe is configured to be attached to a first portion of a digit of the subject, and
wherein the cuff is configured to be attached to a second portion of the digit, the second portion being located on a fingertip side with respect to the first portion.

17. The sensor according to claim 16, wherein:
the cuff is configured for acquiring a non-invasive blood pressure of the subject, and
the probe is configured for acquiring a blood light absorber concentration in the subject.

* * * * *